US00PP24789P3

(12) United States Plant Patent
Danziger

(10) Patent No.: US PP24,789 P3
(45) Date of Patent: Aug. 19, 2014

(54) *IMPATIENS* PLANT NAMED 'DHAR329'

(50) Latin Name: *Impatiens hawkeri*
Varietal Denomination: DHAR329

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 13/694,923

(22) Filed: Jan. 17, 2013

(65) Prior Publication Data

US 2014/0201876 P1 Jul. 17, 2014

(51) Int. Cl.
*A01H 5/00* (2006.01)

(52) U.S. Cl.
USPC ..... Plt./318.6

(58) Field of Classification Search
USPC ..... Plt./318.6
See application file for complete search history.

*Primary Examiner* — Anne Grunberg
(74) *Attorney, Agent, or Firm* — Cassandra Bright

(57) ABSTRACT

A new and distinct *Impatiens* cultivar named 'DHAR329' is disclosed, characterized by large violet flowers. The new variety has good branching, and is sun resistant. The new variety is a *Impatiens*, normally produced as an outdoor garden or container plant.

2 Drawing Sheets

Figure 1:
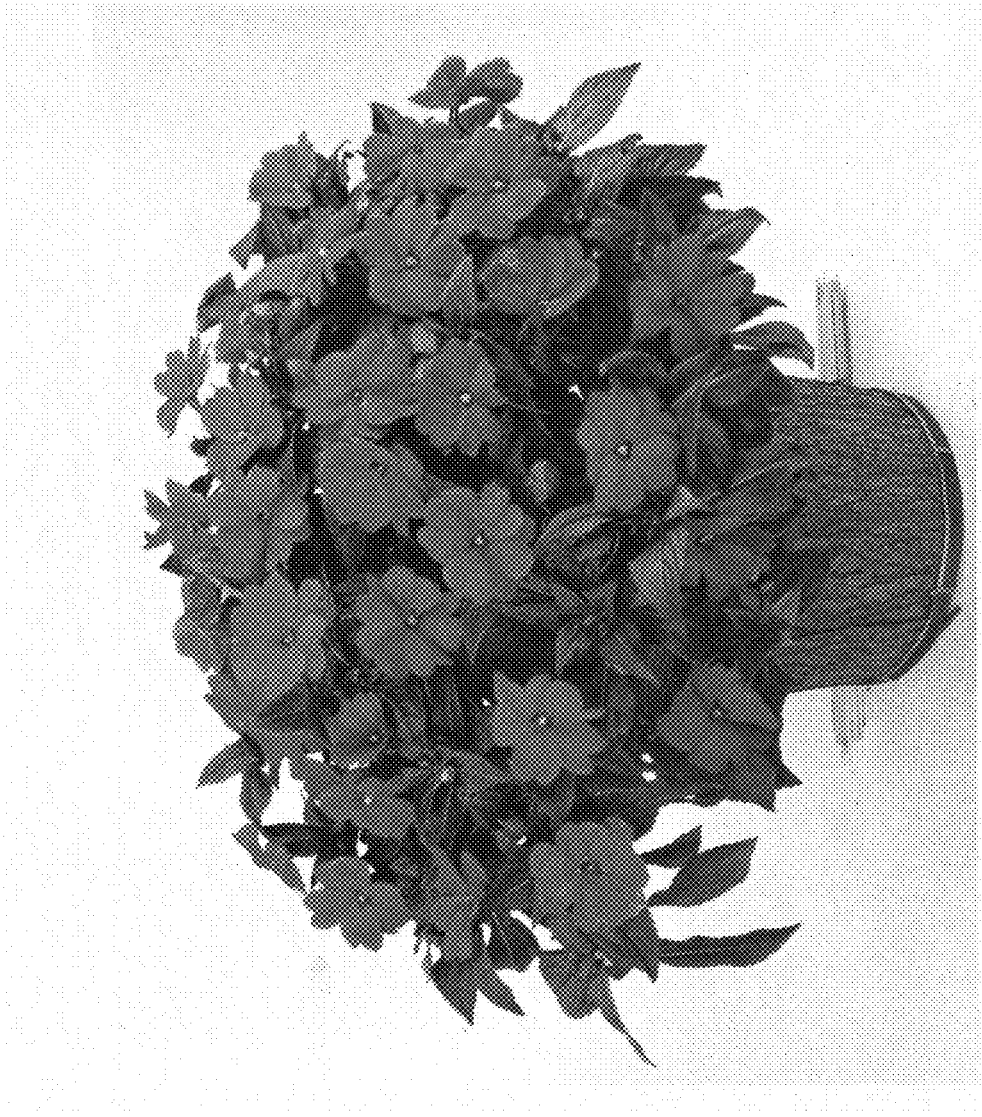

Latin name of the genus and species: *Impatiens hawkeri*.
Variety denomination: 'DHAR329'.

BACKGROUND OF THE INVENTION

The new *Impatiens* cultivar is a product of a planned breeding program conducted by the inventor, Gavriel Danziger, in Moshav Mishmar Hashiva, Israel. The objective of the breeding program was to produce new *Impatiens* varieties for ornamental commercial applications. The cross resulting in this new variety was made during July of 2009.

The seed parent is the unpatented, proprietary seedling variety referred to as *Impatiens hawkeri* '2807' The pollen parent is the unpatented, proprietary seedling variety referred to as *Impatiens hawkeri* '1803'. The new variety was discovered in July of 2010 by the inventor in a group of seedlings resulting from the 2009 crossing, in a research greenhouse in Moshav Mishmar Hashiva, Israel.

Asexual reproduction of the new cultivar was performed by leaf cuttings. The cuttings are from an apical bud that has no more than two expanded leaves and three to four immature leaves present. This was first performed at a research greenhouse in Moshav Mishmar Hashiva, Israel in July of 2010 and has shown that the unique features of this cultivar are stable and reproduced true to type in successive generations.

SUMMARY OF THE INVENTION

The cultivar 'DHAR329' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DHAR329' These characteristics in combination distinguish 'DHAR329' as a new and distinct *Impatiens* cultivar:

1. Large flower size.
2. Violet flower color.
3. Good branching.
4. A sun resistant plant.

Plants of the new cultivar 'DHAR329' are similar to plants of the seed parent, *Impatiens hawkeri* 'NG-Z-116' in most horticultural characteristics, however, plants of the new cultivar 'DHAR329' are more vigorous in growth habit and have darker foliage than the seed parent. 'DHAR329' also produces a violet flower whereas the seed parent produces a white flower.

Plants of the new cultivar 'DHAR329' are similar to plants of the pollen parent; *Impatiens hawkeri* 'NG-8-7741' in most horticultural characteristics, however, plants of the new cultivar 'DHAR329' produce smaller flowers and are more vigorous growth in habit than the pollen parent.

COMMERCIAL COMPARISON

Plants of the new cultivar 'DHAR329' are comparable to the variety *Impatiens* 'Sunpatiens Vigorous Magenta' U.S. Plant Pat. No. 17,662. The two *Impatiens* varieties are similar in most horticultural characteristics; however, the new variety 'DHAR329' differs in having larger, darker colored flowers and a more compact growth habit than the comparator.

Plants of the new cultivar 'DHAR329' can also be compared to the commercial variety *Impatiens* 'Sunpatiens Compact Magenta' U.S. Plant Pat. No. 21,769. These varieties are similar in most horticultural characteristics; however 'DHAR329' produces a larger flower and is more vigorous in its growth habit.

BRIEF DESCRIPTION OF THE PHOTOGRAPHS

The accompanying photograph in FIG. 1 illustrates in full color a typical plant of 'DHAR329' grown in a greenhouse, in a 16 cm pot. Age of the plant photographed is approximately 14 weeks from a rooted cutting.

Figure 2:
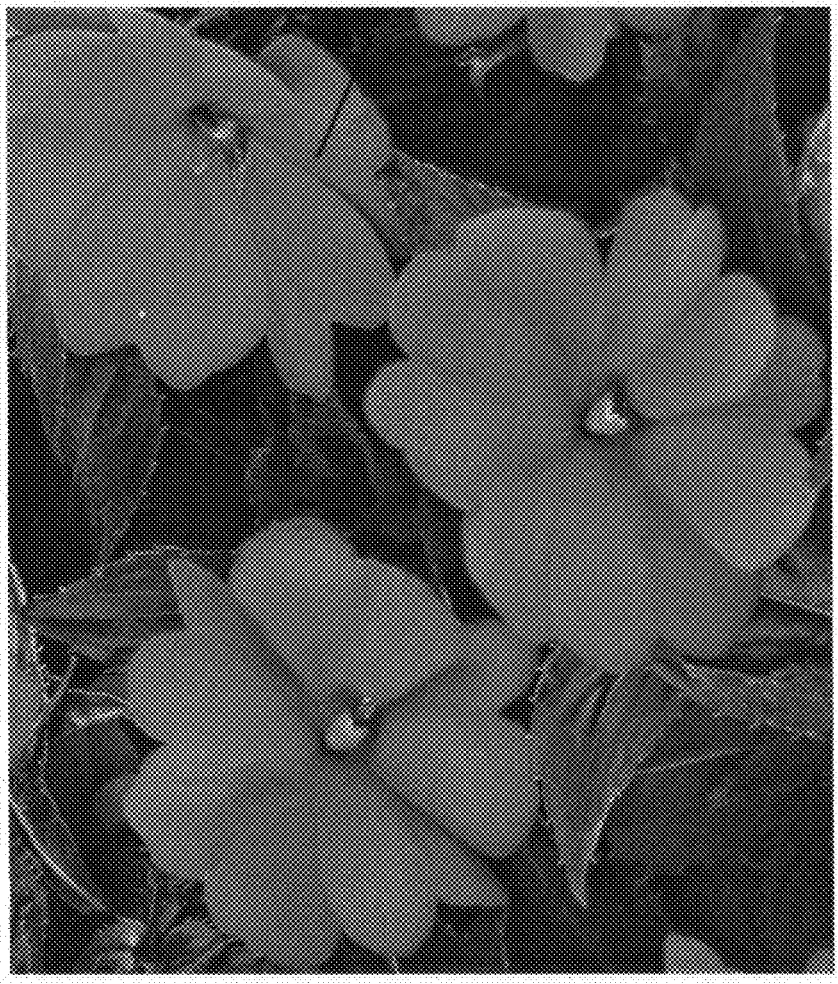

FIG. 2 illustrates in full color a close up of a typical bloom of 'DHAR329'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DHAR329' plants grown outdoors during, Spring, Summer, and Autumn in Moshav Mishmar Hashiva, Israel. The growing temperature ranged from 20° C. to 35° C. during the day and from 15° C. to 25° C. during the night. General light conditions are bright, normal sunlight. Measurements and numerical values represent averages of typical plant types. Botanical classification: *Impatiens hawkeri* 'DHAR329'.

PROPAGATION

Time to initiate roots:
- *Summer*.—About 10 to 12 days at approximately 25° C.
- *Winter*.—About 14 to 20 days at approximately 18° C.

Root description: Fine, adventitious fibrous.

PLANT

Age of plant described: Approximately 14 weeks from rooted cutting.
Pot size of plant described: 16 cm.
Growth habit: Mounded.
Height: 25 cm.
Plant spread: 40 cm.
Growth rate: Vigorous.
Branching characteristics: Highly branched.
Length of primary lateral branches: 23 cm.
Quantity of primary lateral branches: 5-7.
Characteristics of primary lateral branches:
- *Form*.—Oval shape.
- *Diameter*.—1 cm.
- *Color*.—Yellow Green group 146 C RHS.
- *Texture*.—Smooth.
- *Strength*.—Strong, very stable.

Internode length: 6 cm.

FOLIAGE

Leaf:
- *Arrangement*.—Alternate.
- *Quantity*.—Approximately 20-25 per branch.
- *Average length*.—6.5 cm.
- *Average width*.—3 cm.
- *Shape of blade*.—Lanceolate to ovate.
- *Apex*.—Attenuate.
- *Base*.—Acuminate.
- *Margin*.—Ciliate.
- *Texture of top surface*.—Smooth.
- *Pubescence*.—None.
- *Aspect*.—45 degrees.
- *Color*.—Green. Young foliage upper side: Green Group 143 A RHS. Young foliage under side: Yellow Green Group 146 DRHS. Mature foliage upper side: Yellow Green Group 147 A RHS. Mature foliage under side: Yellow Green Group 147 C RHS.
- *Venation*.—Midrib with secondary veins. Pinnate, only lower surface. Type: Pinnate. Venation color upper side: Yellow Green Group 147 C RHS. Venation color under side: Red Group 39 B RHS.
- *Petiole*.—Length: 1 cm. Diameter: 0.5 cm. Color: Yellow Green Group 145 C RHS. Texture: Smooth.

FLOWER

Natural flowering season: Flowers at any day length. All year round in a greenhouse environment. Flowering is continuous from Spring until Fall in an outdoor garden.
Days to flowering from rooted cutting: 10 weeks.
Inflorescence and flower type and habit: Single flowers raised above the foliage. The corolla consists of five petals.
Rate of flower opening: 10 to 15 days from bud to fully opened flower.
Flower longevity on plant: 5-8 Days.
Persistent or self-cleaning: Self cleaning.
Bud:
- *Shape*.—Ovate.
- *Length*.—2 cm.
- *Diameter*.—1 cm.
- *Color*.—Purple Group N78C RHS.

Flower size:
- *Diameter*.—7.5-8 cm.
- *Depth*.—Approximately 1.5 cm.

Petals:
- *Quantity*.—5.
- *Arrangement*.—Overlapping.
- *Length*.—3.5-4 cm.
- *Width*.—4 cm.
- *Shape*.—Obcordate.
- *Apex*.—Obcordate.
- *Base*.—Broad attenuate.
- *Margin*.—Entire.
- *Texture, upper and lower surfaces*.—Smooth.
- *Color*.—Purple. When opening, upper surface: Red Purple Group N74A RHS. When opening, lower surface: Red Purple Group N74B RHS. Fully opened, upper surface: Red Purple Group N74A RHS. Fully opened, lower surface: Purple Pink Group N74C RHS.

Spurs:
- *Quantity per flower*.—1.
- *Length*.—5 cm.
- *Diameter*.—0.1 cm.
- *Aspect*.—Spur curvature 40°-45° from peduncle.
- *Color*.—Towards base: Red Purple Group 59D RHS. Apex: Red Purple Group 59B RHS.

Sepals:
- *Quantity*.—2.
- *Length*.—2 cm.
- *Width*.—1 cm.
- *Shape (overall)*.—Oblong. Apex: Acute. Base: Rounded.
- *Margin*.—Entire.
- *Color*.—Yellow Green Group 145B RHS.

Peduncles:
- *Length*.—4.5-5 cm.
- *Diameter*.—0.5 cm.
- *Angle*.—About 45° to the lateral branch.
- *Strength*.—Stable, flexible.
- *Texture*.—Smooth.

*Color*.—Yellow Green Group 145 D RHS.

Fragrance: None.

REPRODUCTIVE ORGANS

Stamens: There are five stamens with introrse anthers that are more or less fused and form a cap over the ovary.

*Number*.—5.

Anthers:

*Shape*.—Oblong.

*Length*.—Approximately 0.4 cm.

*Color*.—Red Purple Group 72 C RHS.

*Pollen*.—Color: White Group 155 D RHS. Quantity: Few.

Pistil:

*Number*.—1.

*Length*.—0.5 cm.

*Style*.—Length: 0.5 cm. Color: Yellow Green Group 146 C RHS.

*Stigma*.—Shape: Round. Color: White Group N 155B RHS. Ovary Color: Yellow-Green group, RHS 144D RHS.

OTHER CHARACTERISTICS

Seeds and fruits: 5-10 seeds per fruit.

Disease/pest resistance: Common to cultivar.

Temperature tolerance: Tolerant at 30° C. and tolerant at 10° C. degrees Celsius (grows best at 10° C.-30° C.)

What is claimed is:

1. A new and distinct cultivar of *Impatiens* plant named 'DHAR329' as herein illustrated and described.

* * * * *